United States Patent [19]

Esteve Soler

[11] Patent Number: 4,563,452

[45] Date of Patent: Jan. 7, 1986

[54] DERIVATIVES OF OXAZINOBENZOTHIAZINE-6,6-DIOXIDE

[75] Inventor: José Esteve Soler, Barcelona, Spain

[73] Assignee: Provesan S.A., Geneva, Switzerland

[21] Appl. No.: 502,216

[22] Filed: Jun. 8, 1983

[30] Foreign Application Priority Data

Jun. 15, 1982 [FR] France .................. 82 10409

[51] Int. Cl.[4] .................. C07D 417/14; C07D 513/04; A61K 31/535; A61K 31/54
[52] U.S. Cl. .................. 514/222; 544/33; 544/2; 544/3; 544/5; 544/7; 544/8
[58] Field of Search .................. 544/33, 2, 3, 5, 7, 544/8; 424/246; 514/222

[56] References Cited

U.S. PATENT DOCUMENTS

| | | | |
|---|---|---|---|
| 3,492,298 | 1/1970 | Rasmussen | 544/33 |
| 3,855,216 | 12/1974 | Kaminsky et al. | 544/33 |
| 3,923,801 | 12/1975 | Rasmussen | 260/243 |
| 4,378,358 | 3/1983 | Bono | 544/33 |

OTHER PUBLICATIONS

Zinnes et al., J. Med. Chem., 16(1):44-48 (1973).

Primary Examiner—John M. Ford
Attorney, Agent, or Firm—Pennie & Edmonds

[57] ABSTRACT

This invention relates to new derivatives of oxazinobenzothiazine-6,6-dioxide, to a process for the production thereof and to the use thereof as medicaments.

The new derivatives according to the present invention correspond to the general formula I:

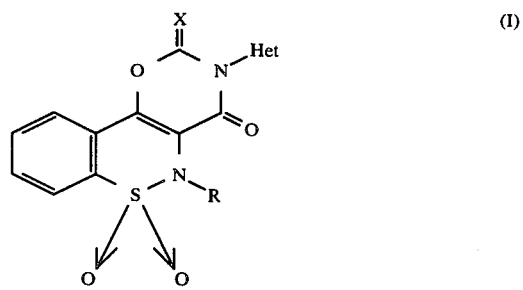

wherein:

R represents a linear or branched lower $C_1-C_4$ alkyl radical, in particular the methyl and ethyl radicals, X represents an oxygen atom or a sulphur atom, and Het represents a mono- or bicyclic unsaturated heterocycle containing a nitrogen heteroatom in the ortho position relative to the link between the said heterocycle and the nitrogen atom of the oxazine ring, the said heterocycle optionally containing one or two other additional heteroatoms selected from nitrogen, oxygen and sulphur, and also being able to be substituted by one or two methyl radicals.

19 Claims, No Drawings

DERIVATIVES OF OXAZINOBENZOTHIAZINE-6,6-DIOXIDE

This invention relates to new derivatives of oxazinobenzothiazine-6,6-dioxide, to a process for the production thereof, and to the use thereof as medicaments.

The new derivatives which are an object of the present invention correspond to the general formula I:

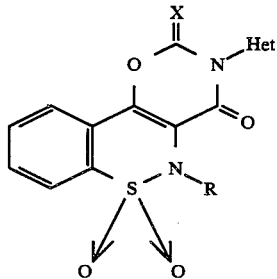

wherein:

R represents a linear or branched lower $C_1$–$C_4$ alkyl radical, in particular the methyl and ethyl radicals, X represents an oxygen atom or a sulphur atom, Het represents a mono- or bicyclic unsaturated heterocycle containing a nitrogen heteroatom in the ortho position relative to the link between the said heterocycle and the nitrogen atom of the oxazine ring, the said heterocycle optionally containing one or two other additional hetero-atoms selected from nitrogen, oxygen and sulphur, and also being able to be substituted by one or two methyl radicals.

The heterocyclic radical Het in the general formula I of the derivatives of the present invention may consist in particular of an unsaturated heteromonocyclic radical containing 5 or 6 ring members. The following radicals are mentioned as particular examples of a radical Het of this type: 2pyridyl; 2-(4-methylpyridyl); 2-(6-methylpyridyl); 2-pyrimidinyl; 5-methyl-3-isoxazolyl; 2-thiazolyl; 4-methyl-2-thiazolyl; 5-methyl-2-thiazolyl; 4,5-dimethyl-2-thiazolyl; 3-isoxazolyl; 5-isoxazolyl; and 5-methyl-1,3,4-thiadiazolyl.

However, the heterocyclic radical Het may also consist of an unsaturated heterobicyclic radical, such as the 2-benzothiazolyl radical.

This invention also relates to a process for the production of the derivatives corresponding to the general formula I defined above. According to the present invention, the derivatives corresponding to the general formula I are produced by reacting 2-alkyl-4-hydroxy-2H-1,2-benzothiazine-1,1-dioxide-3-alkyl carboxylate corresponding to the general formula II

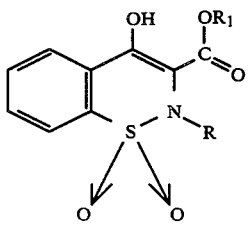

wherein

R and $R_1$ independently represent a linear or branched lower $C_1$–$C_4$ alkyl radical, in particular the methyl and ethyl radicals, with an intermediate compound which is produced in situ and which corresponds to the general formula III:

$$[\text{Het}-\text{N}=\text{C}=\text{O}] \qquad (III)$$

wherein Het is as defined above with respect to the general formula I.

This reaction may be carried out by fusion or in various inert solvents having a high boiling point, for example diethylene glycol dimethyl ether and the like, aromatic hydrocarbons, such as methylnaphthalene or other hydrocarbons, such as Tetralin or Decalin.

The intermediate compound corresponding to the general formula III may in particular be advantageously produced in situ in the reaction medium by thermal decomposition of a urethane derivative corresponding to the general formula IV:

$$\text{Het}-\text{NH}-\overset{\overset{\displaystyle O}{\|}}{\text{C}}-\text{O}-\text{R}_2 \qquad (IV)$$

wherein

Het is as defined above with respect to the general formula I, and $R_2$ represents a phenyl, ethyl, propyl, isopropyl, n-butyl, isobutyl or tert-butyl radical.

The oxazinobenzothiazine-6,6-dioxide derivatives corresponding to the general formula I wherein X represents a sulphur atom are produced from corresponding oxazinobenzothiazine-6,6-dioxide derivatives of the general formula I wherein X represents an oxygen atom by a reaction with a thiation agent, i.e., an agent which is capable of replacing a

double bond by a

double bond, for example being selected from $P_2S_5$ and 2,4-bis-(4-methoxyphenyl)-2,4-dithioxo-1,3,2,4-dithiadiphosphetane.

In consideration of their good anti-inflammatory and analgesic activity and their very low toxicity, the derivatives corresponding to the general formula I are useful as medicaments which may be used in human or animal therapeutics. Thus, this invention also relates to the use of these derivatives as medicaments, as well as to pharmaceutical compositions which contain the derivatives as an active principle.

The production of some derivatives corresponding to the general formula I will now be described in the following by way of simple, non-limiting example.

EXAMPLE 1

Production of 5-ethyl-3-(2-pyridyl)-2H,5H-1,3-oxazino[5,6-c][1,2]benzothiazine-2,4-(3H)dione-6,6-dioxide 4.4 g (0.015 mols) of 2-ethyl-4-hydroxy-2H-1,2-benzothiazine-1,1-dioxide-3-ethyl carboxylate and 3.5 g (0.016 mols) of 2-phenoxycarbonylaminopyridine in 40 ml of diethylene glycol dimethyl ether are heated under reflux at 161° C., under a nitrogen atmosphere, for 30 minutes. The mixture is cooled to ambient temperature and the contents are poured onto 150 ml of water. The precipitate which is obtained is filtered and washed with water. After recrystallisation in acetone, 3.0 g (54%) of 5-ethyl-3-(2-pyridyl)-2H,5H-1,3-oxazino[5,6-c][1,2]benzothiazine-2,4-(3H)dione-6,6-dioxide are obtained which correspond to the formula:

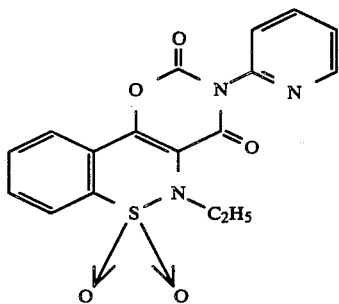

M.p.: 268°-270° C.

Spectroscopic data: IR (KBr): 1185; 1355; 1415; 1635; 1705; 1795 cm$^{-1}$ $^1$H NMR, δ,[DMSO(d$_6$)]: 1.08 (t,3H); 3.75 (q, 2H); 7.43 (e, 2H); 7.86 (e, 5H); 8.4 (d, 1H).

EXAMPLE 2

Production of
5-methyl-3-(2-pyridyl)-2H,5H-1,3-oxazino[5,6-c][1,2]benzothiazine-2,4-(3H)dione-6,6-dioxide

Variant A 14.1 g (0.05 mols) of 2-methyl-4-hydroxy-2H-1,2-benzothiazine-1,1-dioxide-3-ethyl carboxylate and 11.8 g (0.055 mols) of 2-phenoxycarbonylaminopyridine are heated up to fusion in a silicone bath at 210° C. under a nitrogen atmosphere. The fusion is maintained for 10 minutes by distilling the phenol under reduced pressure (25 mm of Hg). The residue is dissolved in acetone, from which crystallize 12.1 g (68%) of 5-methyl-3-(2-pyridyl)-2H,5H-1,3-oxazino[5,6-c][1,2]benzothiazine-2,4-(3H)dione-6,6-dioxide corresponding to the formula:

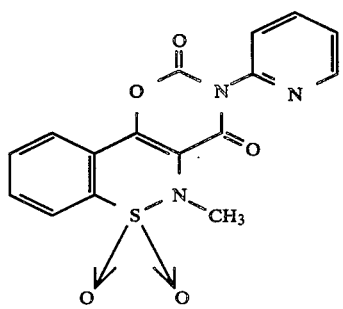

M.p: 259°-261° C.

Spectroscopic data: IR (KBr): 1185; 1355; 1410; 1640; 1710; 1790 cm$^{-1}$ $^1$H NMR, δ, [DMSO(d$_6$)]: 3.02 (s, 3H); 7.52 (e, 2H); 7.92 (3, 5H); 8.52 (d, 1H).

Variant B 2.7 g(0.01 mol) of 2-methyl-4-hydroxy-2H-1,2-benzothiazine-1,1-dioxide-3-methyl carboxylate and 2.1 g (0.011 mols) of 2-t-butoxycarbonylaminopyridine in 30 ml of 1-methylnaphthalene are heated at 200° C. for 15 minutes under a nitrogen atmosphere. The mixture is cooled and precipitated with petroleum ether. After recrystallising in acetone, 1.9 g (55%) of 5-methyl-3-(2-pyridyl)-2H,5H-1,3-oxazino [5,6-c][1,2]benzothiazine-2,4-(3H)dione-6,6-dioxide are obtained which have a melting point of from 257° to 259° C.

Spectroscopic data: IR (KBr): 1185; 1355; 1410; 1640; 1710; 1790 cm $^{-1}$ $^1$H NMR, δ, [DMSO(d$_6$)]: 3.02 (s, 3H); 7.52 (3, 2H); 7.92 (e, 5H); 8.52 (d, 1H).

EXAMPLE 3

Production of
5-methyl-3-(2-pyridyl)-2H,5H-1,3-oxazino[5,6-c][1,2]benzothiazine-2(3H)thione-4-one-6,6-dioxide 8.1 g (0.02 mols) of 2,4-bis-(4-methoxyphenyl)-2,4-dithioxo-1,3,2,4-dithiadiphosphetane and 3.6 g (0.01 mol) of 5-methyl-3-(2-pyridyl)-2H,5H-1,3-oxazino[5,6-c][1,2]benzothiazine-2,4-(3H)dione-6,6-dioxide in 80 ml of xylene are maintained under reflux at 140° C. for 36 hours. The mixture is subjected to chromatography over a column containing silica gel as the stationary phase by initially eluting with xylene and then with chloroform. 1.4 g (38%) of 5-methyl-3(2-pyridyl)-2H,5H-1,3-oxazino[5,6-c][1,2]benzothiazine2(3H)thione-4-one-6,6-dioxide corresponding to the following formula are recovered from the chloroform solution:

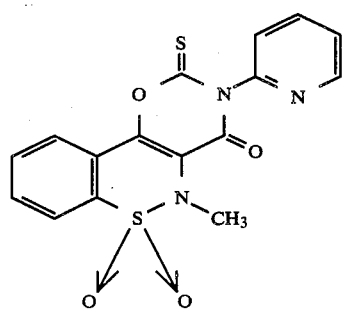

After recrystallisation in acetone, the derivative which is obtained has a melting point of from 269°-271° C.

Spectroscopic data: IR (KBr): 1190; 1320; 1355; 1400; 1640; 1712 cm$^{-1}$ $^1$H NMR, δ, [DMSO(d$_6$)]: 3.05 (s, 3H); 7.54 (e, 2H); 7.92 (e, 5H); 8.48 (d, 1H).

EXAMPLE 4

Production of 5-methyl-3-[3-(5-methyl isoxazolyl)]-2H,5H-1,3-oxazino[5,6-c][1,2]benzothiazine-2,4-(3H)dione-6,6-dioxide 2.8 g (0.01 mols) of 2-methyl-4-hydroxy-2H-1,2-benzothiazine-1,1-dioxide-3-ethyl carboxylate and 2.4 g (0.011 mols) of 3-phenoxy-carbonylamino-5-methyl-isoxazole in 40 ml of 1-methylnapthalene are heated at 200° C. for 15 minutes under a nitrogen atmosphere. The mixture is cooled and precipitated with petroleum ether. It is then recrystallised in acetone and 2.2 g (61%) of 5-methyl-3-[3-(5-methyl-isoxazolyl]-2H,5H-1,3-oxazino[5,6-c][1,2]benzothiazine-2,4-(3H)dione-6,6-dioxide corresponding to the following formula are obtained:

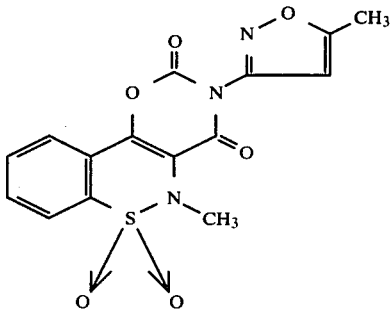

M.p.: 268°–269° C.
Spectroscopic data:
IR (KBr): 1185; 1360; 1400; 1640; 1715; 1788 cm$^{-1}$ $^1$H NMR, δ, [DMSO(d$_6$)]: 2.5 (s, 3H); 3.08 (s, 3H); 6.44 (s, 1H); 7.98 (e, 4H).

EXAMPLE 5

Production of 5-methyl-3-(2-pyrimidinyl)-2H,5H-1,3-oxazino[5,6-c][1,2]benzothiazine-2,4-(3H)dione-6,6-dioxide 2.8 g (0.01 mols) of 2-methyl-4-hydroxy-2H-1,2-benzothiazine-1,1-dioxide-3-ethyl carboxylate and 2.4 g (0.011 mols) of 2-phenoxycarbonylaminopyrimidine in 30 ml of diethylene glycol dimethyl ether are heated under reflux at 161° C. for 30 minutes under a nitrogen atmosphere. The mixture is cooled to ambient temperature and poured onto 100 ml of water. The precipitate which is obtained is filtered, washed with water, agitated with acetone to boiling and re-filtered. 1.8 g (50%) of 5-methyl-3-(2-pyrimidinyl)-2H,5H-1,3-oxazino[5,6-c][1,2]benzothiazine-2,4-(3H)dione-6,6-dioxide corresponding to the following formula are obtained:

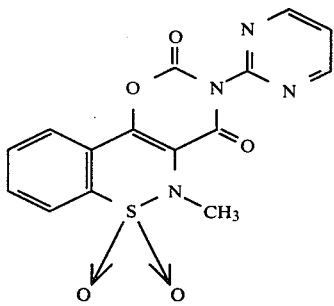

M.p.: 282°–284° C.
Spectroscopic data:
IR (KBr): 1180; 1355; 1400; 1632; 1710; 1787 cm$^{-1}$ $^1$H NMR, δ, [DMSO(d$_6$)]: 3.05 (s,3H); 7.93 (e, 5H); 8.95 (d, 2H).

EXAMPLE 6

Production of 5-methyl-3-[2-(4-methyl pyridyl]-2H,5H-1,3-oxazino[5,6-c][1,2]benzothiazine-2,4-(3H)dione-6,6-dioxide 2.7 g (0.01 mol) of 2-methyl-4-hydroxy-2H-1,2-benzothiazine-1,1-dioxide-3-methyl carboxylate and 2.3 g (0.011 mols) of 2-t-butoxycarbonylamino-4-methylpyridine are heated to fusion in a silicone bath at 160° C. under a nitrogen atmosphere. Fusion is maintained for 5 minutes. The residue is dissolved in acetone, from which crystallise 2.3 g (62%) of 5-methyl-3-[2-(4-methyl pyridyl)]-2H,5H-1,3-oxazino[5,6-c][1,2]benzothiazine-2,4-(3H)dione-6,6-dioxide corresponding to the formula:

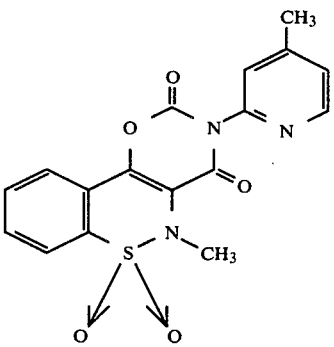

M.p.: 259°–261° C.
Spectroscopic data: IR (KBr): 1195; 1360; 1415; 1640; 1720; 1795 cm$^{-1}$ $^1$H NMR, δ, [DMSO(d$_6$)]: 2.42 (s, 3H); 3.1 (s,3H); 7.4 (e, 2H); 7.98 (e, 4H); 8.4 (d, 1H).

EXAMPLE 7

Production of 5-methyl-3-[2-(6-methyl pyridyl)]-2H,5H-1,3-oxazino[5,6-c][1,2]benzothiazine-2,4-(3H)dione-6,6-dioxide 2.8 g (0.01 mol) of 2-methyl-4-hydroxy-2H-1,2-benzothiazine-1,1-dioxide-3-ethyl carboxylate and 2.3 g (0.011 mols) of 2-t-butoxycarbonylamino-6-methyl-pyridine are heated to fusion in a silicone bath at 160° C. under a nitrogen atmosphere. Fusion is maintained for 5 minutes. The residue is dissolved in acetone from which crystallise 1.5 g (41%) of 5-methyl-3-[2-(6-methyl pyridyl)]-2H,5H-1,3-oxazino[5,6-c][1,2]benzothiazine-2,4-(3H)dione-6,6-dioxide corresponding to the formula:

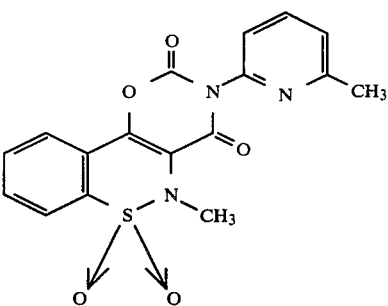

M.p.: 248°–250° C.
Spectroscopic data: IR (KBr): 1190; 1360; 1410; 1640; 1715; 1790 cm$^{-1}$ $^1$H NMR, δ, [DMSO(d$_6$)]: 2.43 (s, 3H); 3.0 (s, 3H); 7.4 (e, 2H); 7.97 (e, 5H).

ANTI-INFLAMMATORY ACTIVITY (INHIBITION OF OEDEMA PRODUCED BY CARRAGEENIN)

Method developed by Winter (Winter, C. A., Risley, E. A. and Nuss, G. W. Proc. Soc. Exp. Biol. Med., 11, 544–540 (1962)).

Male rats of the Sprague-Dawley HC/CEY strain are used, weighing from 90 to 110 g. The products are administered suspended in 5% gum arabic, by an oral method using an oesophageal probe, 1 hour before a subplantar injection in the right foot of each animal of 0.1 ml of 1% carrageenin suspension in physiological serum (NaCl 0.9%). The control animals are given 5% gum arabic, the total volume which is used in every case amounting to 10 ml/kg.

The volume of each foot is measured immediately before the carrageenin injection (time 0), then three and five hours after this injection using a mercury plethysmograph.

The inflammation index is calculated for each animal after 3 hours ($I_3$) and after 5 hours ($I_5$) after the carrageenin injection by means of the following formulae:

$$I_3 = \frac{V_3}{V_0} \times 100 \quad I_5 = \frac{V_5}{V_0} \times 100$$

wherein:

$V_O$=volume of the foot at time zero (immediately before the administration of carrageenin)

$V_3$=volume of the foot 3 hours after the injection of carrageenin $V_5$=volume of the foot 5 hours after the injection of carrageenin.

The average inflammation index is calculated for the control batch after 3 hours ($It_3$) and after 5 hours ($It_5$).

The percentage of inhibition of the oedema (anti-inflammatory activity) is calculated for each animal by means of the formulae:

$$A_3 = \frac{(It_3 - I_3)}{(It_3 - 100)} \times 100 \quad A_5 = \frac{(It_5 - I_5)}{(It_5 - 100)} \times 100$$

wherein:

$A_3$=anti-inflammatory activity in percentage of inhibition of the oedema after 3 hours $A_5$=anti-inflammatory activity in percentage of inhibition of the oedema after 5 hours.

The anti-inflammatory activity is proportional to the logarithm of the administered dose. The dose which reduces the volume of the odema by 25% is obtained from the curve of dose logarithm-% effect. This dose is adopted as ED-50, since the maximum effect which is achieved is the reduction of the oedema by 50%.

The following Table I reproduces the results which were obtained with the derivatives of the previously described Examples.

TABLE I

| Product | ED-50 in mg/kg p.o. | |
|---|---|---|
| | 3 hours | 5 hours |
| Example 1 | >40 | >40 |
| Example 2 | 2.3 | 2.6 |
| Example 3 | >40 | >40 |
| Example 4 | 38 | 39 |
| Example 5 | >40 | >40 |
| Example 6 | >40 | >40 |
| Example 7 | 20 | 25 |
| Phenylbutazone | 17 | 17 |

Analgesic activity with respect to the pain induced by acetyl choline

Method developed by Collier (Collier, H. O. W. Dinneen, L. C. Johnson, C. A. and Schneider, C.—Br. J. Pharmac. Chemother., 32, 295–310 (1968)).

Male mice of the Swiss strain are used, weighing from 20 to 25 g. The mice are put into individual cages. A volume of 0.2 ml/20 g of a solution of acetyl choline bromide of 0.32 mg/ml is administered intraperitoneally to each animal. Thus, the injected dose of acetyl choline bromide is 3.2 mg/kg. The number of contortions or stretches performed by each mouse is counted over a period of 5 minutes. After 5 minutes, the products are administered using 5% gum arabic as a vehicle. After 40 and 120 minutes of administration of the products, another injection of acetyl choline is given and the number of contortions which are observed over a period of 5 minutes is counted.

The percentage of inhibition of the number of contortions after 40 and 120 minutes is calculated for each animal using the following formulae:

$$A_{40} = \left(\frac{N_O - N_{40}}{N_O}\right) \times 100 \quad A_{120} = \left(\frac{N_O - N_{120}}{N_O}\right) \times 100$$

wherein:

$N_O$=number of contortions before the product is administered $N_{40}$=number of contortions 40 minutes after administration of the product $N_{120}$=number of contortions 120 minutes after administration of the product.

The percentage of inhibition of the contortions is directly proportional to the logarithm of the administered dose. The dose which reduces the number of contortions to half the initial value (ED-50) is obtained from the curve of dose logarithm-% effect.

The following Table II reproduces the results which were obtained with the derivatives of the previously described Examples.

TABLE II

| Product | ED-50 in mg/kg p.o. | |
|---|---|---|
| | 40 min. | 120 min. |
| Example 1 | >160 | >160 |
| Example 2 | 1.8 | 1.1 |
| Example 3 | 25 | 25 |
| Example 4 | 154 | 154 |
| Example 5 | >160 | >160 |
| Example 6 | >160 | >160 |
| Example 7 | 7.5 | 10 |
| Phenylbutazone | 40 | 35 |

Inhibition of the Prostaglandin-Synthetase of Seminal Vesicle of Cattle

Method developed by Yoshimoto (Yoshimoto, A., Ito, H. and Tomita, K.—J.Biochem., 68, 487 (1970).

The activity of the prostaglandin-synthetase (1.14.99.1) is determined by measuring the increases in absorbance at 278 nm due to the formation of prostaglandin B from prostaglandin E in an alkaline medium.

The incubation temperature was 37±0.1° C. in every case. The process which is used is put into practice as follows.

0.5 ml of substrate solution (0.6 mg of arachidonic acid in 10 ml of buffer) and 0.5 ml of buffer are added to 1.5 ml of cofactor solution (0.55 mg of hydroquinone+0.5 mg of hemoglobin+7.7 mg of glutathione in 12 ml of 0.2M Tris-HCl buffer of pH 8.0), containing 10 mg of enzyme, and the mixture is incubated at 37° C. for 10 minutes. The enzymatic reaction is stopped by the addition of 1.5 ml of 0.2M citric acid and the pGE is extracted with 2×5 ml of ethyl acetate. The organic phase is evaporated under a stream of nitrogen at 40° C. and the residue is redissolved in 2 ml of methanol and 0.5 ml of 3M potassium hydroxide. Finally, the absorptions at 278 nm are measured with respect to a blank to which 0.5 ml of buffer are added instead of 0.5 ml of substrate solution.

The enzymatic activity is expressed as an increase in the optical density for 10 minutes of reaction.

The inhibition exerted by phenylbutazone and, for example, by the derivative corresponding to Example 2 on the prostaglandin-synthetase is determined by maintaining the enzyme in contact with the products for 5 minutes. The method is as follows.

0.5 ml of different solutions of phenylbutazone or of the derivative of Example 2 are added to 1.5 ml of cofactor solution, containing 10 mg of enzyme, and the mixture is maintained at 37° C. for 5 minutes, whereafter 0.5 ml of substrate solution are added and the incubation is maintained for an additional 10 minutes at the same temperature.

The subsequent stages are identical to those which have already been described. The relation between the increase in optical density of the experiments with and without inhibitor is the value of the percentage of inhibition.

Table III indicates for phenylbutazone and the derivative of Example 2, the concentrations which produce an inhibition of 50%.

TABLE III

| Inhibition of the prostaglandin-synthetase (1.14.99.1) by phenylbutazone and the derivative of Example 2, in vitro | |
|---|---|
| Product | IC$_{50}$ (M) |
| Phenylbutazone | 3 × 10$^{-4}$ |
| Example 2 | 1 × 10$^{-4}$ |

Acute Toxicity

Method developed by Litchfield and Wilcoxon (Litchfield, J. T. and Wilcoxon, E.—J. Pharmacol. Exp. Therap., 96, 19–113 (1949)).

The product is administered orally suspended in 5% gum arabic. The administered volume is 25 ml/kg in the case of mice and 10 ml/kg for rats. The LD-50 is calculated according to the mentioned method. The results which are obtained for the derivative of Example 2 are given in the following Table IV.

TABLE IV

| Species | Sex | LD-50 (mg/kg) v.o. |
|---|---|---|
| Mouse | ♂ | 6 192 |
| | ♀ | 8 841 |
| Rat | ♂ | 1 434 |
| | ♀ | 1 994 |

Bearing in mind their good pharmaco-dynamic properties, the oxazinobenzothiazine-6,6-dioxide derivatives according to the present invention may be used in a satisfactory manner in human and animal therapeutics, in particular in the treatment of acute or chronic disorders which require the use of anti-inflammatory and/or analgesic agents, for example disorders such as arthritis deformans, osteoarthritis, spondylitis, acute musculoskeletal alterations and acute gout.

In human therapeutics, the administration dose of the derivatives of the present invention of course depends on the gravity of the disorder to be treated. It will generally be from about 40 to about 100 mg per day. The derivatives of this invention will be administered, for example in the form of tablets, capsules or suppositories.

Three particular galenical forms of the derivatives, which are an object of the present invention, will now be indicated in the following by way of example.

| Example of capsule formula | |
|---|---|
| 5-methyl-3-(2-pyridyl)-2H,5H—1,3-oxazino [5,6-c] [1,2] benzothiazine-2,4-(3H) dione-6,6-dioxide | 0.020 g |
| Lactose | 0.136 g |
| Talc | 0.0016 g |
| Magnesium stearate | 0.0016 g |
| Aerosil-200 | 0.0008 g |
| Capsule weight | 0.160 g |
| Example of tablet formula | |
| 5-methyl-3-(2-pyridyl)-2H,5H—1,3-oxazino [5,6-c] [1,2] benzothiazine-2,4-(3H) dione-6,6-dioxide | 0.020 g |
| Avicel pH 102 | 0.016 g |
| Lactose | 0.055 g |
| Primojel | 0.003 g |
| Polyvinylpyrrolidone | 0.005 g |
| Magnesium stearate | 0.001 g |
| Tablet weight | 0.100 g |
| Example of suppository formula | |
| 5-methyl-3-(2-pyridyl)-2H,5H—1,3-oxazino [5,6-c] [1,2] benzothiazine-2,4-(3H) dione-6,6-dioxide | 0.050 g |
| Monolene | 1.950 g |
| Suppository weight | 2.000 g |

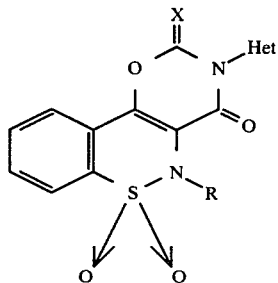

I claim:
1. A compound of the formula

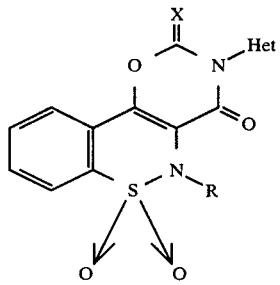

wherein:
R is a linear of branched lower C$_1$–C$_4$ alkyl radical,
X is a oxygen atom or a sulphur atom, and
Het is a 5 or 6 membered monocyclic unsaturated, unsubstituted heterocycle or heterocycle substituted with one or two methyl radicals and containing a nitrogen heteroatom in the ortho position relative to the link between the heterocycle and the nitrogen in the oxazine ring and in which other member of the heterocycle are carbon, oxygen, nitrogen or sulphur.

2. The compound according to claim 1, wherein the heterocycle is substituted with one or two methyl radicals.

3. The compound according to claim 1, wherein Het is selected from the group consisting of 2-pyridyl; 2-(4-methyl pyridyl); 2-(6-methyl pyridyl); 2-pryimidinyl; 5-methyl-3-isoxazolyl; 2-thiazolyl; 4-methyl-2-thiazolyl; 5-methyl-2-thiazolyl; 4,5-dimethyl-2-thiazolyl; 3-isoxazolyl; 5-isoxazolyl; and 5-methyl-1,3,4-thiadiazolyl.

4. The compound according to claim 1, which is 5-ethyl-3-(2-pyridyl)-2H,5H-1,3-oxazino[5,6-c][1,2]benzothiazine-2,4-(3H)dione-6,6-dioxide.

5. The compound according to claim 1, which is 5-methyl-3-(2-pyridyl)-2H,5H-1,3-oxazino [5,6-c][1,2]benzothiazine-2,4-(3H)dione-6,6-dioxide.

6. The compound according to claim 1, which is 5-methyl-3-(2-pyridyl)-2H,5H-1,3-oxazino[5,6-c][1,2]benzothiazine-2(3H)thione-4-one-6,6-dioxide.

7. The compound according to claim 1, which is 5-methyl-3-[3-(5-methyl isoxazolyl)]-2H,5H-1,3-oxazino [5,6-c][1,2]benzothiazine-2,4-(3H)dione 6,6-dioxide.

8. The compound according to claim 1, which is 5-methyl-3-(2-pyrimidinyl)-2H,5H-1,3-oxazino[5,6-c][1,2]benzothiazine-2,4-(3H)dione-6,6-dioxide.

9. The compound according to claim 1, which is 5-methyl-3-[2-(4-methyl pyridyl)]-2H,5H-1,3-oxazino[5,6-c][1,2]benzothiazine-2,4-(3H)dione-6,6-dioxide.

10. The compound according to claim 1, which is 5-methyl-3-[2-(6-methyl pyridyl)]-2H,5H-1,3-oxazino[5,6-c][1,2]benzothiazine-2,4-(3H)dione-6,6-dioxide.

11. A compound of the formula

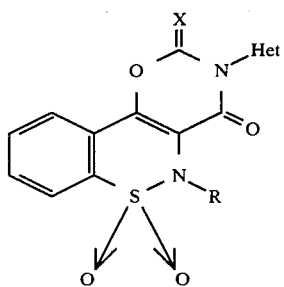

wherein:
R is a linear or branched lower $C_1$–$C_4$ alkyl radical,
X is an oxygen atom or a sulphur atom, and
Het is 2-benzothiazolyl.

12. An anti-inflammatory and analgesic composition comprising a compound according to claim 1 or 11, and a pharmaceutically acceptable carrier therefor.

13. The anti-inflammatory and analgesic composition according to claim 12, wherein the composition is formulated as a tablet.

14. The anti-inflammatory and analgesic composition according to claim 12, wherein the composition is formulated as a capsule.

15. The anti-inflammatory and analgesic composition according to claim 12, wherein the composition is formulated as a suppository.

16. A method for treating acute or chronic inflammation, comprising administering to a human or an animal an effective anti-inflammatory amount of a compound according to claim 1 or 11.

17. A process for the production of a compound of the formula

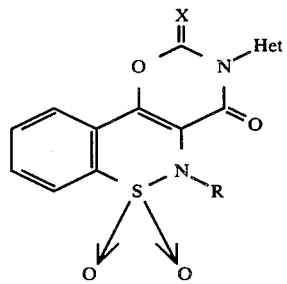

wherein:
R is a linear or branched lower $C_1$–$C_4$ alkyl radical,
X is an oxygen atom, and
Het is a 5 or 6 membered monocyclic unsaturated, unsubstituted heterocycle or heterocycle substituted with one or two methyl radicals and containing a nitrogen heteroatom in the ortho position relative to the link between the heterocycle and the nitrogen in the oxazine ring and in which other members of the heterocycle are carbon, oxygen, nitrogen or sulphur comprising:
reacting a compound of the formula

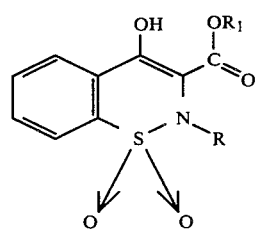

wherein
R is defined as above
$R_1$ is a linear or branched lower $C_1$–$C_4$ alkyl radical, with an intermediate compound of the formula

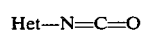

wherein Het is defined as above, and wherein the intermediate compound is produced in situ by thermal decomposition of a urethane derivative of the formula

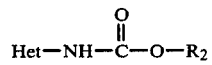

wherein:
Het is defined as above,
$R_2$ is a radical selected from the group consisting of phenyl, ethyl, propyl, isopropyl, n-butyl, isobutyl, and tert-butyl radicals.

18. The process according to claim 17, wherein R and $R_1$ are selected from the group of consisting of methyl and ethyl radicals.

19. A process for the production of a compound of the formula wherein:

R is a linear or branched lower $C_1$–$C_4$ alkyl radical,

X is an oxygen atom, and

Het is 2-benzothiazolyl comprising:

reacting a compound of the formula

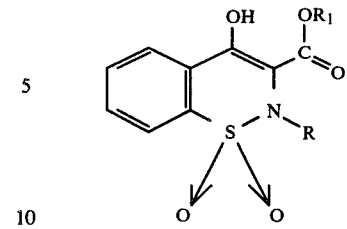

wherein
 R is defined as above
 $R_1$ is a linear or branched lower $C_1$–$C_4$ alkyl radical,
with an intermediate compound of the formula Het—N=C=O wherein Het is as defined above and wherein the intermediate compound is produced in situ by thermal decomposition of a urethane derivative of the formula

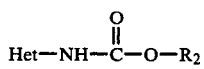

wherein
 Het is defined as above, and
 $R_2$ is a radical selected from the group consisting of phenyl, ethyl, propyl, isopropyl, n-butyl, isobutyl and tert-butyl radicals.

* * * * *